US006602703B2

(12) United States Patent
Dutil

(10) Patent No.: US 6,602,703 B2
(45) Date of Patent: Aug. 5, 2003

(54) PHOTOBIOREACTOR

(75) Inventor: Frédéric Dutil, Québec (CA)

(73) Assignee: CO₂ Solution Inc., Val-Belair (CA)

( * ) Notice: Subject to any disclaimer, the term of this patent is extended or adjusted under 35 U.S.C. 154(b) by 0 days.

(21) Appl. No.: 10/195,260

(22) Filed: Jul. 12, 2002

(65) Prior Publication Data

US 2003/0073231 A1 Apr. 17, 2003

(30) Foreign Application Priority Data

Oct. 17, 2001 (CA) ............................................. 2359417

(51) Int. Cl.⁷ ............................................. C12M 1/00
(52) U.S. Cl. ........................ 435/292; 15/88; 15/104.04; 165/95; 165/DIG. 4; 435/420
(58) Field of Search ............................. 435/292.1, 410, 435/420; 210/602, 610, 719, 757; 15/104.04, 246, 88; 165/95, DIG. 4

(56) References Cited

U.S. PATENT DOCUMENTS

| 4,952,511 A | 8/1990 | Radmer ....................... 435/314 |
| 5,104,803 A | 4/1992 | Delente ....................... 435/287 |
| 5,137,828 A | 8/1992 | Robinson et al. ............ 435/296 |
| 5,169,051 A | 12/1992 | Noé ............................ 228/5.7 |
| 5,242,827 A | 9/1993 | Chaumont et al. .......... 435/287 |
| 5,447,629 A | 9/1995 | Chaumont et al. .......... 210/96.1 |
| 5,614,378 A | 3/1997 | Yang et al. .................... 435/41 |
| 5,846,816 A | 12/1998 | Forth ....................... 435/292.1 |
| 6,110,370 A * | 8/2000 | Van Hille et al. ........... 210/602 |
| 6,174,720 B1 | 1/2001 | Oxley et al. ............. 435/293.1 |
| 2003/0059932 A1 | 3/2003 | Craigie et al. ........... 435/292.1 |

FOREIGN PATENT DOCUMENTS

| CA | 1187826 | 5/1985 | ............ C12M/1/36 |
| CA | 1207695 | 7/1986 | ............ C12M/1/00 |
| CA | 1228559 | 10/1987 | ............ C12M/1/00 |
| CA | 2036885 | 8/1992 | ............ C12N/1/12 |
| CA | 2204921 | 11/1998 | ............ C12N/1/12 |

* cited by examiner

Primary Examiner—David A. Redding
(74) Attorney, Agent, or Firm—Ware, Fressola, Van Der Sluys & Adolphson LLP

(57) ABSTRACT

A photobioreactor is disclosed for cultivating a photosynthetic organism. This photobioreactor provides innovative features that allow an easy cleaning of the light source. The photobioreactor has a container for containing a liquid culture medium for cultivating photosynthetic organisms, light-emitting tubes mounted within the container. The photobioreactor also has cleaning devices mounted within the container for cleaning the outer surface of the light-emitting tubes and actuators for actuating the cleaning devices.

29 Claims, 8 Drawing Sheets

PHOTOBIOREACTOR

FIELD OF THE INVENTION

The present invention relates generally to the field of photobioreactors. More particularly, it concerns a photobioreactor, a culture unit and a process for cultivating photosynthetic organisms, such as microalgae.

BACKGROUND OF THE INVENTION

The algae biomass artificially produced is usually dried and used as a nutraceutical food for humans. Derived fine biochemical products can be extracted from algae, for instance, cosmetic pigments, fatty acids, antioxidants, proteins with prophylactic action, growth factors, antibiotics, vitamins and polysaccharides. The algic biomass can also be useful, in a low dose, to replace or decrease the level of antibiotic in animal food or be useful as a source of proteins. Furthermore, the algic biomass provided in a wet form, as opposed to a dried form, can be fermented or liquefied by thermal processes to produce fuel. The algae biomass which may have commercial interests are: *Spirulina maximum, Spirulina platensis, Dunaliella salina, Botrycoccus braunii, Chlorella vulgaris, Chlorella pyrenoidosa, Serenastrum capricornutum, Scenedesmus auadricauda*, Anabaenopsis, Aulosira, Cylindrospermum, and Tolypothrix.

Various approaches of algae production are known in the art. A first generation of photobioreactors is based on the use of shallow lagoons agitated with one or several paddle wheels. The photobioreactors of this first generation have the disadvantage of offering poor productivity vs the seasonal and daily climatic variations and are thus to be confined to tropical and subtropical areas. They also have the disadvantage of being prone to contamination.

Other approaches of algae production have emerged over the past years. An example, is the use of closed cultivating systems which have gained popularity because they overcame the majority of the limitations allotted to the conventional shallow lagoons. The most popular closed cultivating systems are the tubular photobioreactors whose configuration allows to reach high production rates due to the optimization of their light path, their temperature control and their culture mixture. This second generation of photobioreactors allows for an automated control and a more effective absorption of $CO_2$ used as a source of carbon. It also allows the pH of the culture medium to be lowered. Examples of tubular photobioreactors are shown in U.S. Pat. Nos. 5,137,828; 5,242,827 and 6,174,720.

The photobioreactors of the first and second generations were constructed to principally receive the sun's daylight. Their productivity is indeed limited to the intensity of the sun, which intensity depends on the photoperiod, the season, the localization and the diurnal cycle. It is possible to provide an artificial light to compensate for the periods of low intensity. However, in such a case, the energy losses are numerous. The fact that these types of photobioreactors are being laid out outside, even under a greenhouse, also limits their use in more moderate climatic areas.

The use of artificial light as an energy source for the growth of microalgae was the subject of several studies and gave birth to the third generation of photobioreactors. Photobioreactors of various shapes and employing various systems of artificial lighting are known in the art. Examples of these photobioreactors are given in U.S. Pat. Nos. 5,104,803; 5,169,051 and 5,614,378. Because their scaling was too expensive, the photobioreactors of the third generation rarely exceeded the stage of prototype. Furthermore, a major drawback with these photobioreactors, is that they become dirty or contaminated unless special precautions are taken. Indeed, adhesions of microalgae occur in a natural manner, particularly on the walls where light is emitted. The extent of this phenomenon is a function of the cultured algae species, as well as the constituent material of the light-emitting devices and the culturing conditions. This effect of adhesion of microalgae leads to a reduction in the volume of culture exposed to the light. It also increases the risks of contamination as a result of the development of bacteria and/or protozoa, which develop in the absence of light.

On an other hand, it is now of general knowledge that the main gas causing the greenhouse effect and the reheating of the planet is the carbon dioxide ($CO_2$). This gas comes from various sources. $CO_2$ of anthropic origin is emitted by breathing, fossil combustion of fuel and by certain chemical processes. It is also shown that the inorganic carbon provided in the form of gaseous $CO_2$ or of bicarbonate can be useful as the only source of carbon for the growth of the microalgae. The gaseous $CO_2$ is generally directly injected into the culture medium at concentrations reaching 15%, the balance consisting of air. Though more expensive, the bicarbonate, generally provided in the form of sodium bicarbonate, is another source of inorganic carbon assimilable by the microalgae.

Several drawbacks were identified concerning the coupling of techniques involving the sequestration by the microalgae of $CO_2$ of anthropic origin. The most important drawbacks are the dependence on the light intensity of the sun, the external temperature, the large surfaces occupied by basins of low yield culture and the $CO_2$ absorption towers.

Although many photobioreactors have been proposed in the prior art, there is still a need for an improved photobioreactor using artificial light as the energy source for photosynthesis. Indeed, there is a need for a photobioreactor designed so as to reduce or eliminate the problem described above concerning the accumulation of microalgae on the light-emitting source. There is also a need for a photobioreactor that can easily be coupled with techniques involving the recycling of $CO_2$ of anthropic origin.

SUMMARY OF THE INVENTION

An object of the present invention is to provide a photobioreactor that satisfies at least one of the above-mentioned needs.

According to the present invention that object is achieved with a photobioreactor comprising a container for containing a liquid culture medium for cultivating photosynthetic organisms, and a plurality of parallel light-emitting tubes mounted within the container and extending in a first direction, each light-emitting tube having an outer surface. The photobioreactor further comprises cleaning means mounted within the container for cleaning the outer surface of the light-emitting tubes, and actuating means for actuating the cleaning means.

Thanks to the cleaning means provided within the container and the actuating means for actuating the same, it is possible with the present invention to easily get rid of the cultivated organisms which may block the light source by adhering to the same. Also, the simplicity of its concept makes it a very attractive and easy tool to be used for growing a desired organism at a substantially low cost.

According to another aspect of the invention, there is provided a culture unit for cultivating photosynthetic organisms, comprising a photobioreactor for cultivating a photosynthetic organism in a liquid culture medium and a bioreactor for producing bicarbonate ions and hydrogen ions from a $CO_2$-containing gas, the bioreactor comprising:

a reaction chamber containing immobilized carbonic anhydrase or analog thereof capable of catalyzing the hydration of dissolved $CO_2$ into the bicarbonates ions and hydrogen ions, a liquid inlet in fluid communication with the reaction chamber, for receiving a liquid, a gas inlet in fluid communication with the reaction chamber, for receiving a $CO_2$-containing gas; and a liquid outlet in fluid communication with the reaction chamber, for dispensing a liquid solution containing the bicarbonates ions and hydrogen ions.

The culture unit further comprises means for transferring the solution of bicarbonates ions and hydrogen ions dispensed from the liquid outlet to the photobioreactor.

As can be appreciated, one advantage of a culture unit as defined above is that it allows the use, at low cost, of bicarbonate ions as the source of carbon necessary for the growth of the organisms. Also, thanks to the use of a $CO_2$-containing gas in the bioreactor, the unit has the advantage of reducing $CO_2$ contained in the air. Consequently, it also helps reducing the greenhouse effect mentioned above.

The invention also proposes a process for producing photosynthetic organisms, the process comprising the steps of:

a) cultivating a photosynthetic organism in a photobioreactor as defined above, and thereby obtaining a liquid culture medium containing photosynthetic organisms;

b) removing from the photobioreactor a portion of the liquid culture medium; and c) separating the liquid culture medium of step b) into a solid phase containing the photosynthetic organisms and a liquid phase.

BRIEF DESCRIPTION OF THE DRAWINGS

These and other objects and advantages of the invention will become apparent upon reading the detailed description and upon referring to the drawings in which.

DESCRIPTION OF PREFERRED EMBODIMENTS

Figure 1:
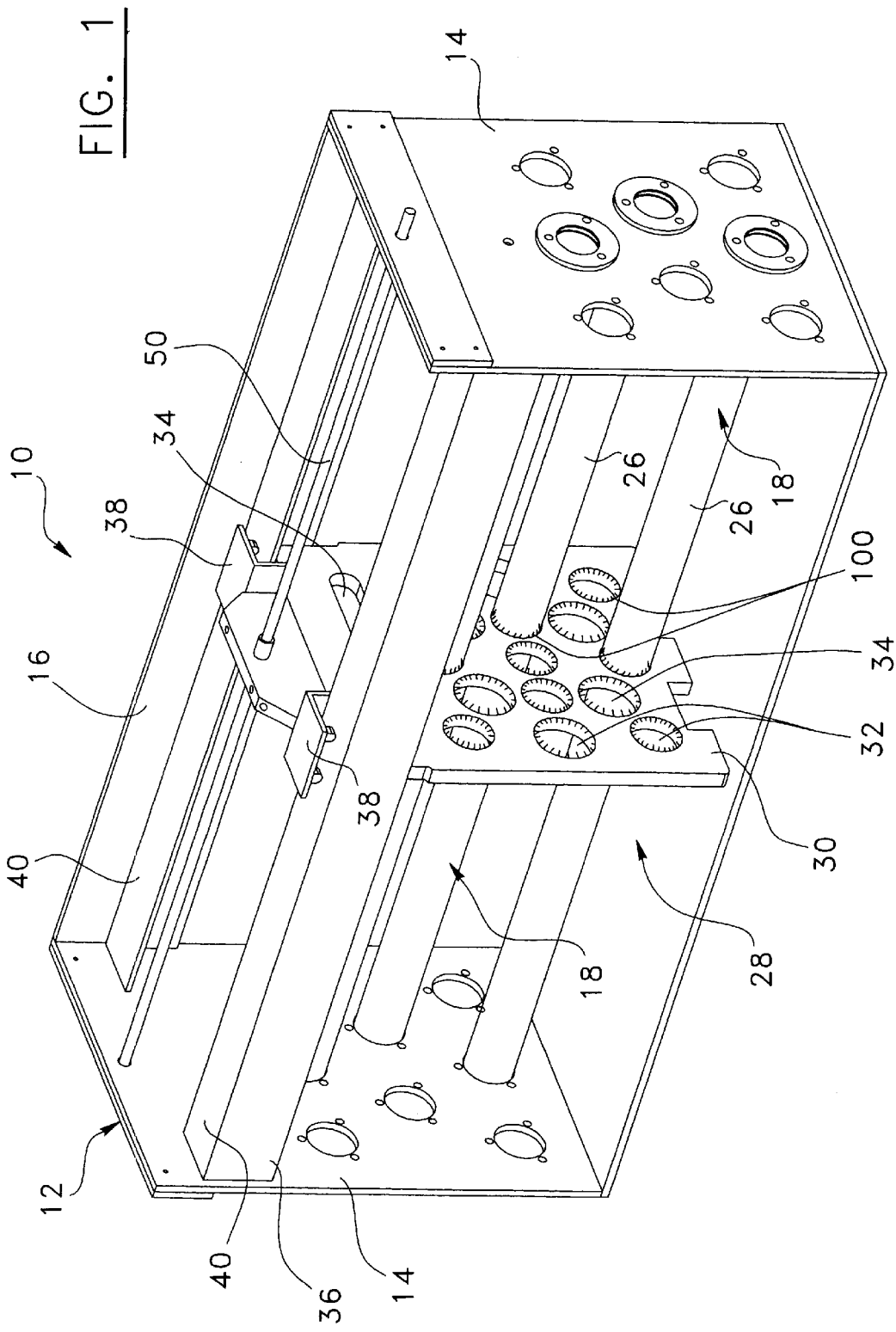
FIG. 1 is a perspective view of a photobioreactor according to a first preferred embodiment of the invention, with one side wall removed to better see the inside of the photobioreactor.

As shown in the drawings and in accordance with a first aspect of the invention, a photobioreactor for cultivating photosynthetic organisms is proposed. The photobioreactor of the invention is suitable for the culture of any kind of photosynthetic organism, such as plant cells and unicellular or multicellular microorganisms having a light requirement. As used herein, the term "photosynthetic organisms" also includes organisms genetically modified by techniques well known to one skilled in the art.

Figure 2:
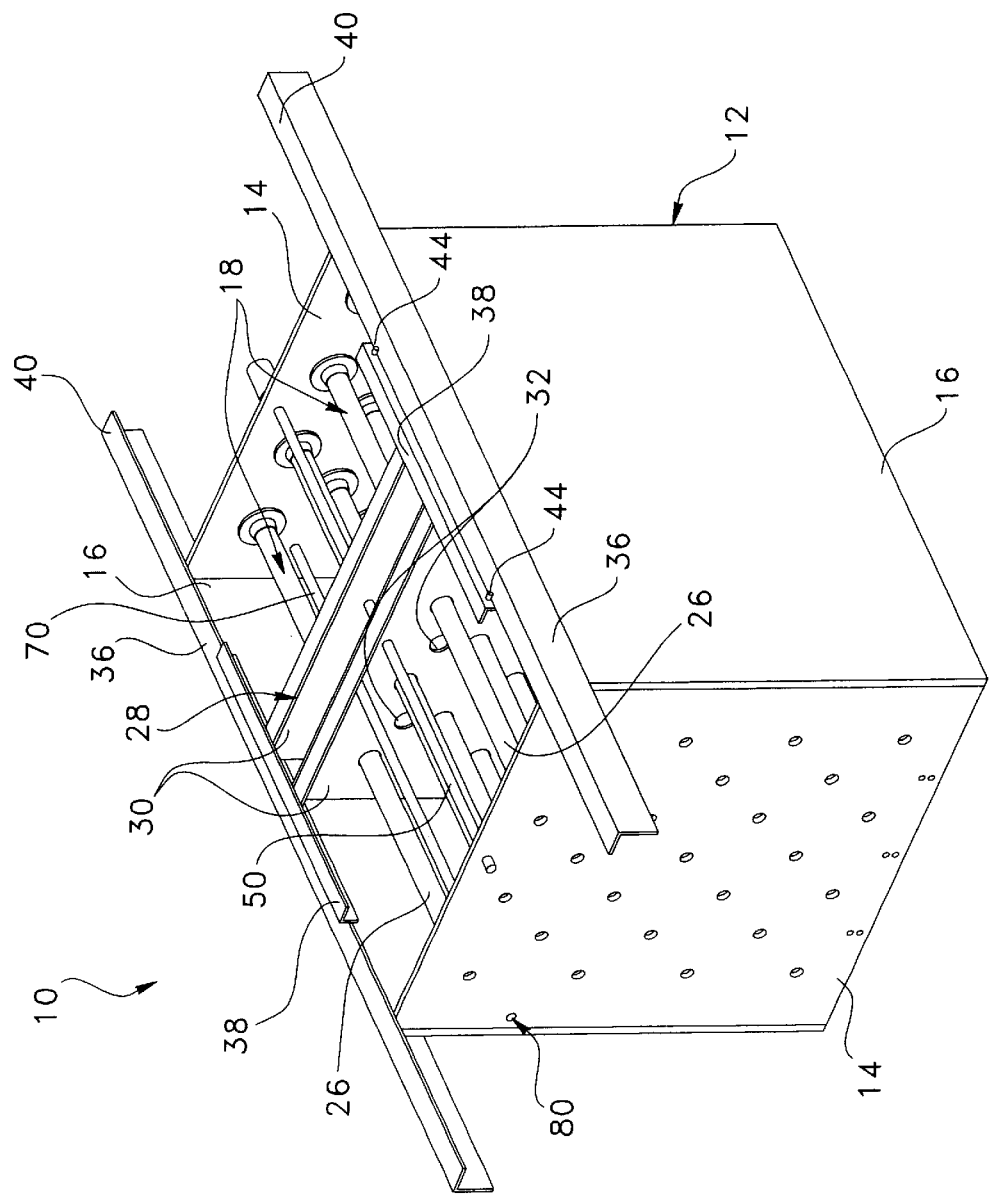
FIG. 2 is a perspective view of a photobioreactor according to a second preferred embodiment of the invention.

Referring now to FIGS. 1 and 2, the photobioreactor (10) of the present invention comprises a container (12) for containing a liquid culture medium for cultivating photosynthetic organisms. The container (12) has a first and a second pair of opposite sidewalls (14, 16). These sidewalls (14, 16) are preferably made of an inert material such as polyvinyl chloride, high-density polyethylene, low-density polyethylene and polypropylene. Advantageously, a metal framing may be added to solidify the container (12) thus formed if necessary.

Figure 5:
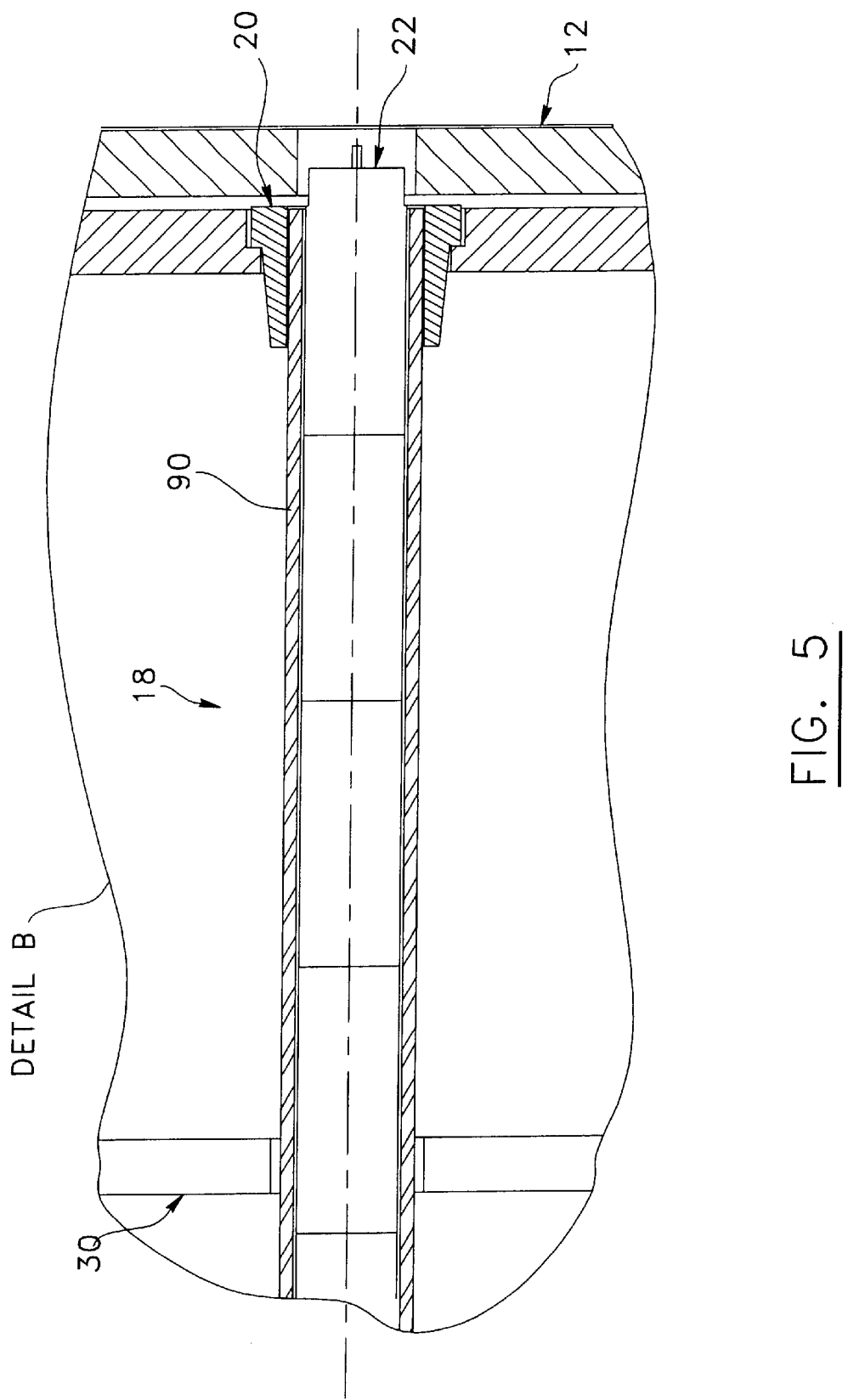
FIG. 5 is an enlarged view of section B of FIG. 4.

The photobioreactor (10) also comprises a plurality of parallel light-emitting tubes (18) mounted within the container (12) and extending in a first direction. In this case, the light-emitting tubes extend between the first pair of sidewalls (14). As best viewed in FIG. 2, the light-emitting tubes (18) are preferably disposed in an equidistant and offset way. The distance between the tubes (18) will depend on the selected cellular density and the desired productivity. For instance, a distance of 6 to 10 cm between the tubes (18) is suggested. Turning now to FIG. 5, each light-emitting tube (18) preferably consists of a casing (90) and a light source (22) inserted therein. As used herein, the term "light source" refers to any types of light tubes (22) which emit light substantially uniformly and radially along their length. For instance, the light tubes (22) may be neon tubes in their "off the shelf" condition which provide or not the light spectrum necessary to photosynthesis. The casing (90) of the light-emitting tubes (18) can be made of any material as long as they are made of a transparent material, such as acrylic. However, in a situation where the photobioreactor (10) has to be sterilized at elevated temperatures (for instance up to 125° C.), it will be understood that one skilled in the art will have the knowledge to chose the suitable materials. For instance, the casing (90) of the light-emitting tubes (18) may be made of glass, whereas the container (12) may be made of stainless steel. Certain polymers which can resist to such elevated temperatures may also be used.

Although the present invention contemplates employing a light-emitting tubes (18) as defined above, a person skilled in the art will understand that the invention is not restricted to this precise type of light-emitting tubes (18). Indeed, it is conceivable to provide a light-emitting tubes (18) which may only consist of a light tube (22). In such a case, appropriate methods well known to one skilled in the art for non-permanently sealing the extremities of the light tube (22) to the container (12) may be used.

Referring again to FIG. 5, the casing (90) of each light-emitting tube (18) is preferably maintained within the container (12) by sealed supports (20) thus allowing an access to the casing (90) of the light-emitting tubes (18) from outside the photobioreactor (10) to insert the light source (22) therein. The casing (90) of the light-emitting tubes (18) preferably has a diameter dimensioned so as to allow an easy insertion of the light source (22). If the distance between the outer surface of the light source (22) and the inner wall of the casing (90) is too great, losses of lighting for the culture will occur. These losses are due to the diffraction of the light on the inner wall of the casing (90) and thus depend on the angle of incidence and on the wavelength (color) of the light beam. This phenomenon causes an undesirable conversion of light energy into thermal energy. If such a case arises, a cooling gas circulating between the light source (22) and the casing (90) may be provided to cool the light source (22).

Referring back to FIGS. 1 and 2, the photobioreactor (10) further comprises cleaning means mounted within the container (12) for cleaning the outer surface (26) of the light-emitting tubes (18) and actuating means for actuating the cleaning means preferably along the entire length of the light-emitting tubes (18). The mechanism of the actuating means will be described further below.

The cleaning means preferably comprises a support frame (28) movable between the first pair of sidewalls (14) of the container (12). The support frame (28) comprises a plurality of cleaning devices (100) adapted to clean the outer surface (26) of the light-emitting tubes (18), as best shown in FIG. 1. It will be understood that there is at least one cleaning device (100) associated with a respective light-emitting tube (18).

In accordance with the first preferred embodiment shown in FIG. 1, the support frame (28) comprises one plate (30) mounted at right angles to the first direction, in other words, the plate (30) is mounted substantially parallel to the first pair of sidewalls (14). The support frame (28) may alternatively comprise more than one plate (30), preferably two, as shown in FIG. 2. In both cases, the plate (30) comprises a plurality of openings (32) each sized and shaped to receive a light-emitting tube (18). Each cleaning device (100), which is preferably a brush made of a plurality of bristles, is located in a respective opening (32). Thus, it will be understood that these openings (32) have a diameter slightly greater than the one of the light-emitting tubes (18) in order to adequately fix the brush (100) on the inside edge of the opening (32). The plate (30) of the support frame (28) is preferably provided with a plurality of through-holes (34), as illustrated in FIG. 1, so as to allow free passage of the culture medium through the plate (30), thus allowing the mixing of the culture medium when the support frame (28) is moved between the first pair of sidewalls (14). A through-hole (34) according to the present invention is not restricted to a specific shape. For instance, the through-holes (34) may be round-, square- or oblong-shaped.

In an embodiment of the invention not illustrated, the support frame (28) of the photobioreactor (10) could simply rest on the bottom floor of the container (12). However, it could be advantageous to provide the photobioreactor (10) with hanging means for hanging the support frame (28) within the container (12) as shown in FIGS. 1 and 2. Such hanging means, among other things, could help reducing or even preventing the friction between the support frame (28) and the bottom floor. The hanging means preferably comprise a pair of opposite support members (36) extending longitudinally in the first direction along the second pair of sidewalls (16). The hanging means also comprises a pair of resting members (38) each adapted to rest on one of the support members (36) and to move along the same (36). The support members (36) preferably comprises a rail (40) mounted along each one of the sidewalls (16). As best viewed in FIG. 6 in conjunction with FIG. 1, a first resting member (38) is provided on an end portion of the top side (42) of the plate (30) and a second one (38) is provided on the other end portion of the top side (42) of the plate (30). In this connection, and in accordance with the first preferred embodiment shown in FIG. 1, it can be appreciated that the support members (36) may be fixed to the first and/or second pairs of sidewalls (14, 16), whereas in the case of the second preferred embodiment shown in FIG. 2, the support members (36) are preferably fixed to the second pair of sidewalls (16).

A person skilled in the art will understand that the way by which the support members (36) and the resting members (38) are fixed to the container (12) could be achieved by gluing or welding together the parts in question or by any other fixing means known to such person. In this connection, it will be clear that the choice of the fixing means will depend on the materials of which the photobioreactor is made of.

Figure 6:
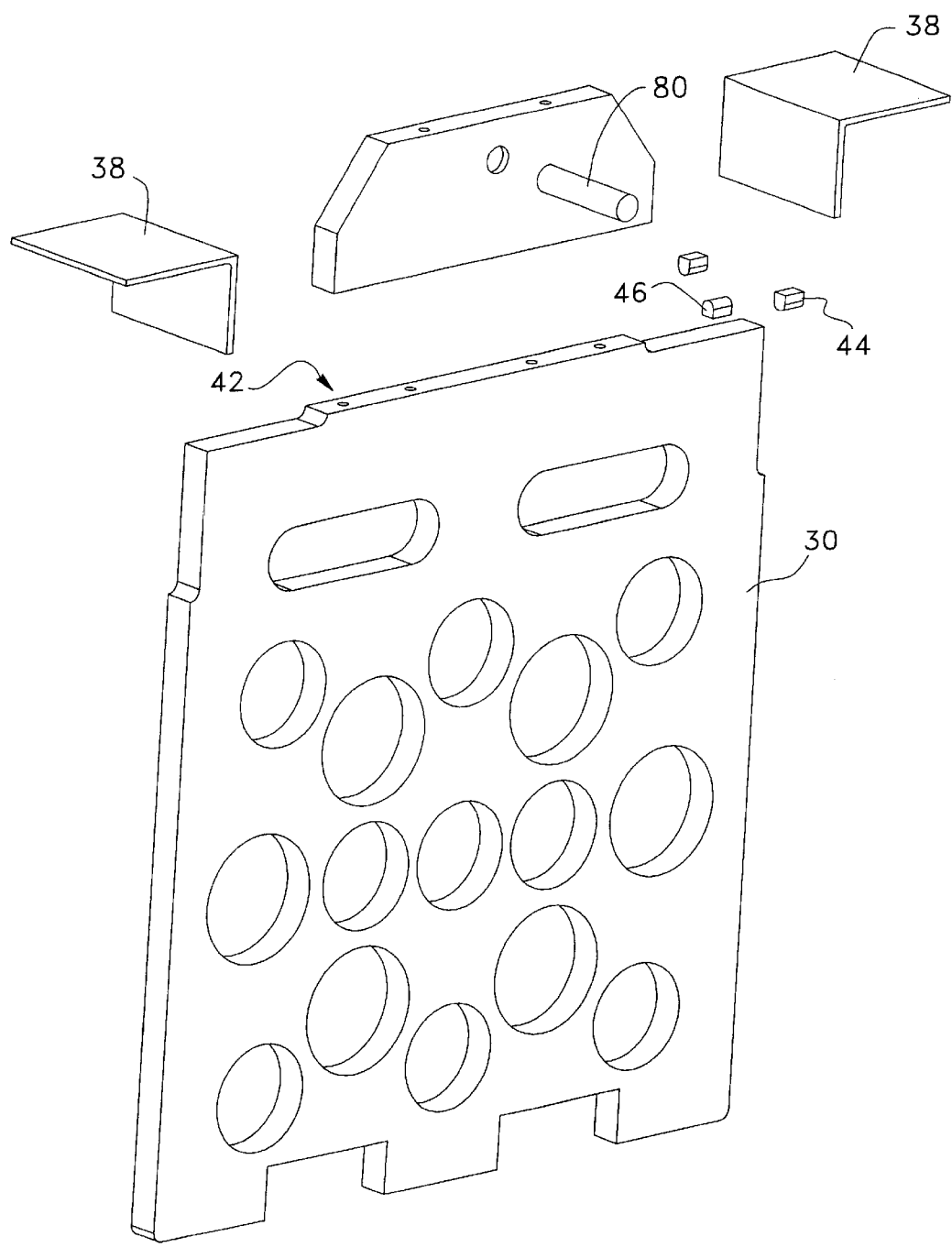
FIG. 6 is an exploded view of the support frame of the photobioreactor of FIG. 1.

In order to adequately allow the resting member (38) to move along its respective rail (40), the resting member (38) is preferably provided with a roller (44), and advantageously with a set of rollers for rolling on the rail (40), as shown in FIG. 2. Moreover, it may be advantageous in certain situations to add rollers to provide a more stabilized rolling movement. In such a case, and as shown in FIG. 6, an additional roller (46) disposed on each end portion of the top side (42) of the plate (30) may be added in order to sandwich the rail between the rollers (44, 46). A person skilled in the art will know the appropriate way of fixing the rollers to their respective location. Such a person will also understand that the means for allowing the resting members (38) to move along its respective rail (40), is not restricted to the use of rollers. For instance, it is conceivable to use devices such as those allowing is a resting member (38) to slide along its respective rail (40). It is further conceivable to modify the configuration or the shape of the resting member (38) so that the latter (38) be in a direct sliding relationship with its respective rail. Of course, in such cases, it is highly preferable that the surface of the device, or the resting member (38) and the rail (40), be made of materials that will facilitate a sliding movement between the parts in question. For example, these parts could advantageously be coated with Teflon®.

As mentioned above and as shown in FIGS. 1 and 2, the support frame (28) is moved between the first pair of sidewalls (14) with the aid of an actuating means. The actuating means preferably comprises a driving endless screw (50) operatively connected to the support frame (28) and a power means (not shown) for inducing a rotation movement to the endless screw (50). As best shown in FIG. 6, a hollow cylinder (80) with a threaded hole, or simply a nut, is mounted to the top side (42) of the plate (30). The cylinder (80) is adapted to receive therein the driving endless screw (50) shown in FIG. 1, and to interact with the same. Since this mechanism is well known, it will not be further explained. As can be appreciated, the rotational movement of the endless screw (50) causes the support frame (28) to move back and forth between the first pair of sidewalls (14). It will be understood that the power means may be any power means suitable to one skilled in the art to move the support frame in a sufficient way. However, a particular power means contemplated by the present invention is a reversible electric motor or a manual driving handle for imparting the rotational movement to the endless screw (50). Therefore, the support frame (28) from a preferable slow back-and-forth translational movement, has a first role of cleaning the outer surface (26) of the light-emitting tubes (18). Secondly, the support frame (28) will indirectly induce the mixing of the culture medium thanks to the presence of the through-holes (32).

Figure 4:
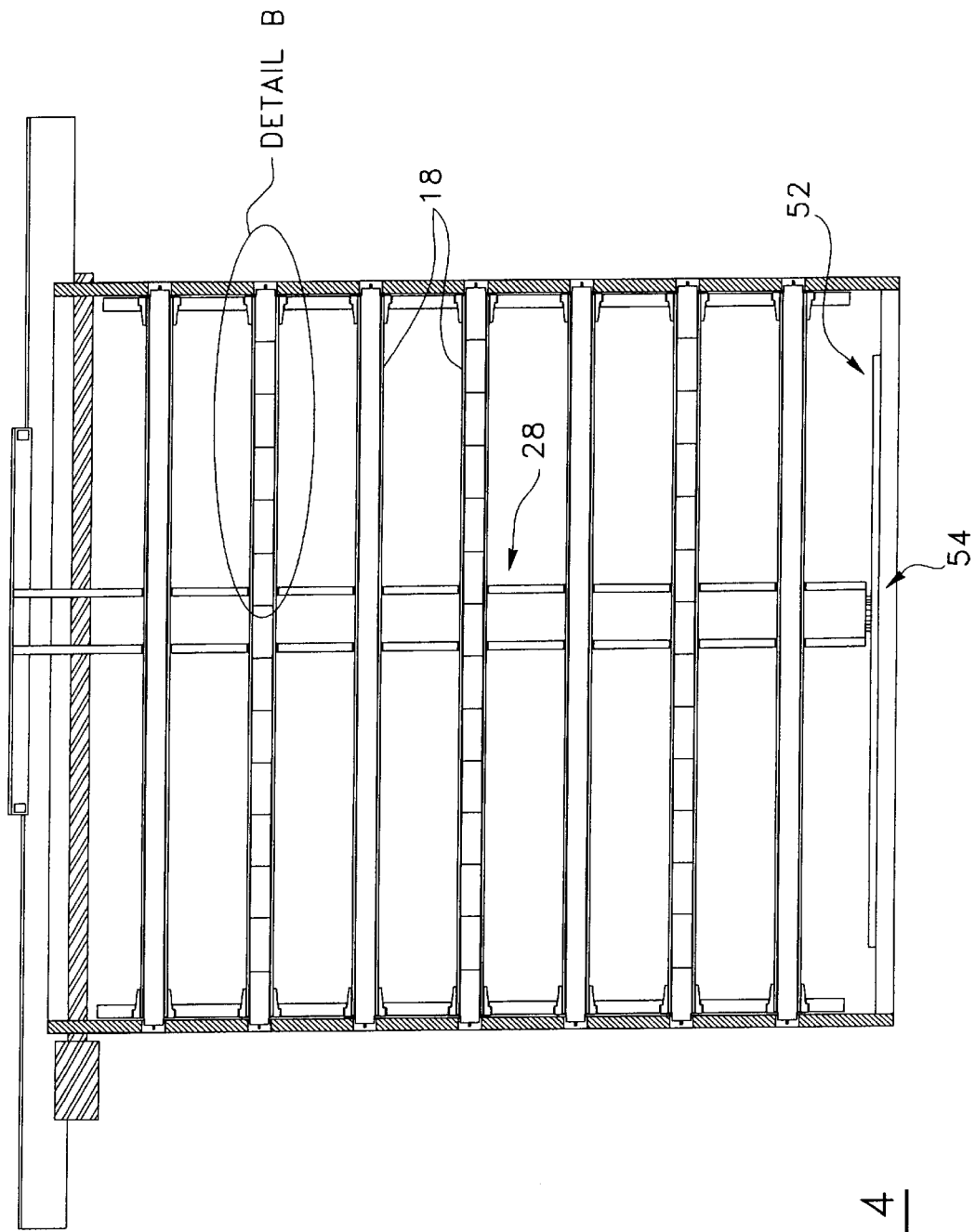
FIG. 4 is a cross-sectional side view taken along the line A—A of FIG. 3.

The movable support frame (28) may further have the task of cleaning a gas dispenser (52) extending on the bottom floor of the container (12). Indeed, the photobioreactor shown in FIGS. 1 and 2, preferably further comprises a gas dispenser (52) for dispensing gaseous $CO_2$ into the culture medium, as shown in FIG. 4. The gas dispenser (52) may comprise at least one dispensing tube (52) spanning generally parallel to the light-emitting tubes (18) underneath the support frame (28). The dispensing tube (52) also preferably comprises a gas inlet for receiving $CO_2$ enriched air and a plurality of gas outlets for dispensing the $CO_2$ enriched air into the container. The dispensing tube (52) is preferably disposed on the bottom of the container (12) in order to take advantage of the fact that as the $CO_2$ is bubbled into the culture medium, it forces the medium to rise, thus improving substantially the mixing of the culture medium and further avoiding a stratification of the cultivated organisms and the accumulation of oxygen which would then cause a decrease of the organism production. In this connection, the support frame (28) preferably comprises brushing means (54) on its bottom edge, such as a plurality of bristles, for brushing the outer surface of the gas dispenser (52).

It will be understood that although the photobioreactor (10) of the present invention preferably has a rectangular configuration (FIG. 1), it is recognized that any suitable shape may be used. For instance, the present invention also contemplates employing a cylindrical-shaped or a cubic-shaped photobioreactor as shown in FIG. 2. For illustrative purposes only, the cubic photobioreactor may have the following dimensions: 1,2 m deep by 1,2 m of width by 1,2 m height for a total working volume of 1,7 cubic meters. In the case of a rectangular photobioreactor, the suggested dimensions are : 1,2 deep by 2,4 m of width by 2,4 m height for a working volume of 6,7 cubic meters. A person skilled in the art will understand that the working culture volume of the photobioreactor (10) can easily be increased by simply modifying the dimensions of its components. Such modifications do not in any way affect the performance or operation of the photobioreactor (10) of the present invention.

Figure 7:
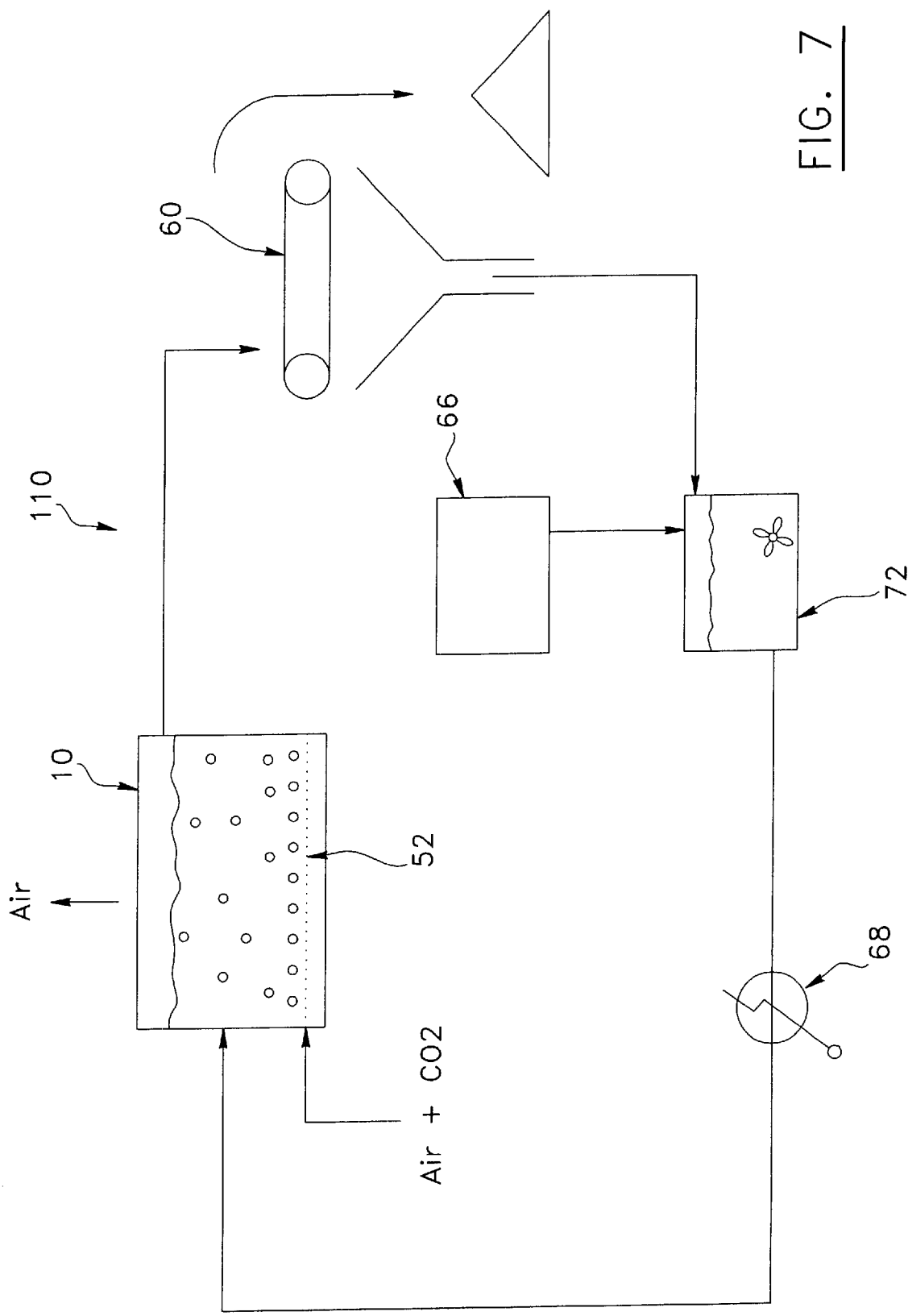
FIG. 7 is a schematic flow chart of a first preferred variant of the process for producing photosynthetic organisms according to the present invention.
Figure 8:
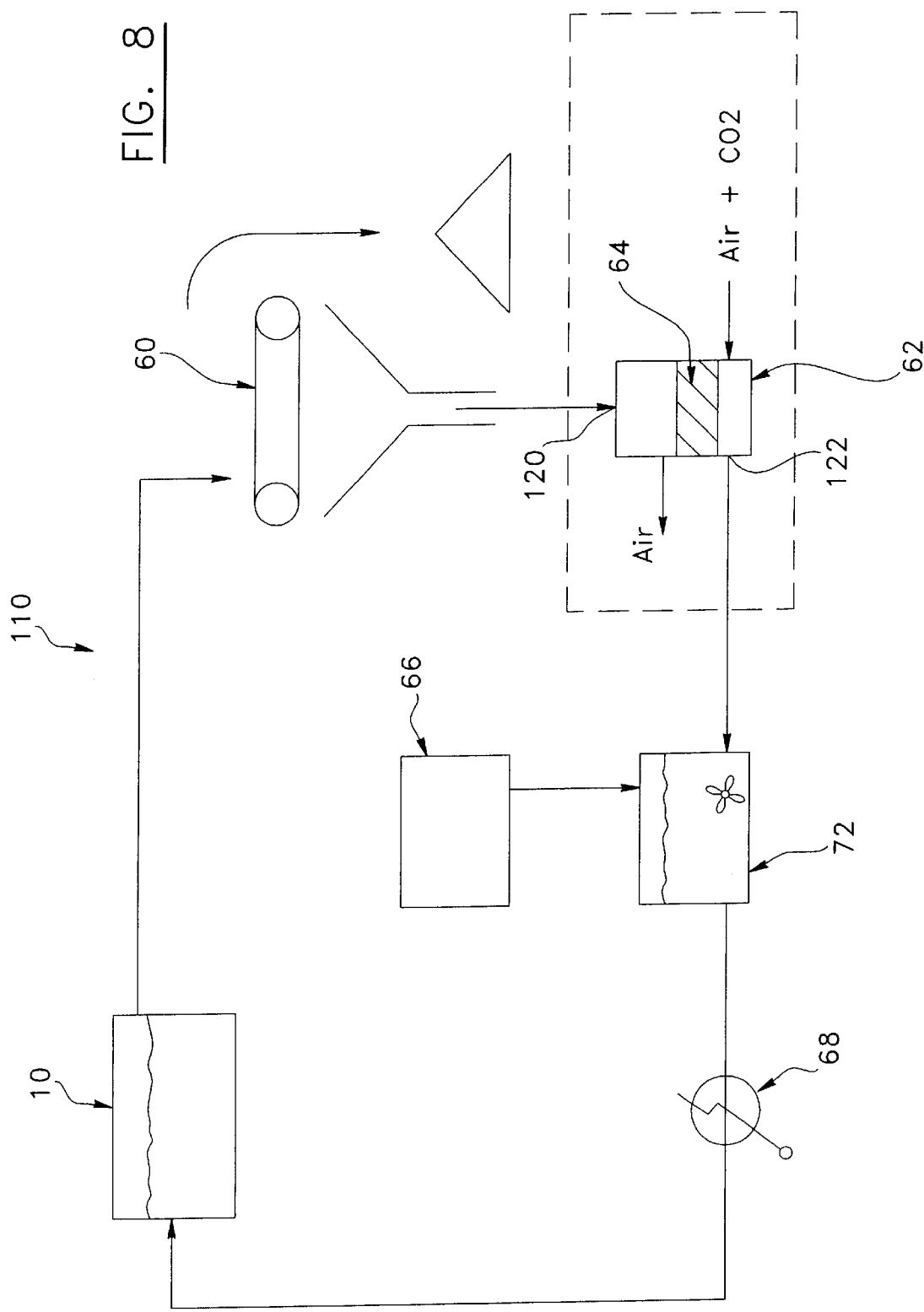
FIG. 8 is a schematic flow chart of a second preferred variant of the process for producing photosynthetic organisms according to the present invention.

According to another aspect of the present invention and as shown in FIGS. 7 and 8, a process for producing photosynthetic organisms is proposed. This process comprises the steps of a) cultivating a photosynthetic organism in a photobioreactor (10) as defined above, and thereby obtaining a liquid culture medium containing photosynthetic organisms; b) removing from the photobioreactor (10) a portion of the liquid culture medium; and c) separating the liquid culture medium of step b) into a solid phase containing the photosynthetic organisms and a liquid phase.

In step b), the liquid culture medium is preferably pumped out from the photobioreactor (10) by means of a conventional pump. The flow rate of the pumped liquid culture medium depends on the cellular density inside the photobioreactor (10). The higher the flow is, the more the productivity will be high. A suggested pumping flow rate ranges between 1 and 2 volumes of liquid culture medium per working volume of the photobioreactor (10) per day.

The separating process (60) of step c) is preferably filtration, flocculation, sedimentation or centrifugation process. In general, the present invention preferably contemplates employing a filter (60), and the separation efficiency will thus depend on the size of the cultivated organisms in relation to the size of the filter's pores. For nonfilamentous organisms that are difficult to filter continuously, the following separation processes are suggested: flocculation, sedimentation or centrifugation. A preferable separation efficiency is obtained when over 90% of the organisms of the pumped liquid culture medium is extracted.

As shown in FIG. 8, the process further preferably comprises the step of producing a solution of bicarbonate ions and hydrogen ions in a bioreactor (62) such as the one described in the international application WO 98/55210 in the name of the applicant. Such a bioreactor (62) comprises a reaction chamber (64) containing immobilized carbonic anhydrase or analog thereof capable of catalyzing the hydration of dissolved $CO_2$ into bicarbonates ions and hydrogen ions. The process preferably further comprises the step of feeding the photobioreactor (10) with the solution of bicarbonates ions and hydrogen ions produced in the bioreactor (62).

In this case, the process further preferably comprises the step of feeding the bioreactor (62) with the liquid phase obtained in step c) described above. In other words, the liquid phase obtained from the separation of the liquid culture medium coming from the photobioreactor (10) could advantageously be fed into the bioreactor (62) as a source of liquid.

In the process, liquid can be lost, for example, by evaporation. Liquid can also be lost during the separation process. In order to compensate for these liquid losts and to maintain the concentration of the nutriments, the process further preferably comprises the step of adding to the solution of bicarbonate ions and hydrogen ions a concentrate of liquid culture medium (66), thereby forming a liquid solution containing the added liquid culture medium and the bicarbonate and hydrogen ions. A person skilled in the art will understand that such concentrate of liquid culture medium comes from a source other than the liquid phase obtained in the above step c). This person of the art will also understand that in order to obtain a homogenous liquid solution, the process of the invention advantageously further has a step of mixing the liquid solution by means of a mixing unit (72). For instance, the mixing unit (72) is preferably a conventional stirrer but it could be any other stirring device known to one skilled in the art. Eventhough, the present invention preferably adds the concentrate of liquid culture medium to the solution of bicarbonate ions and hydrogen ions, it is conceivable to directly add said concentrate to the liquid culture medium of the photobioreactor (10). The person in the art will further understand that the liquid solution could be obtained in a slightly different way. For instance, the liquid phase obtained in step c) could bypass the bioreactor (62), and alternatively be fed into the mixing unit (72) so as to mix altogether the liquid phase, the concentrate of liquid culture medium and the solution of bicarbonates ions and hydrogen ions produced in the bioreactor (62). In such a case, the source of liquid of the bioreactor (62) would have to be provided by other means.

The required feeding rate of said concentrate (66) and the proportion of each nutriment present are determined by the analysis of the liquid culture medium present in the photobioreactor (10) and/or by analyzing the produced organism. The concentrate of culture medium (66) is preferably prepared from low quality mineral salts. The contaminants found in the concentrate (66) such as nitrates, iron, sulfur, zinc, copper, will be used for the organism's growth. Some of the gas contaminants will also be used. This will advantageously decrease the manufacturing costs of the medium. It will also allow the culture medium used in the process to be recycled.

The process further preferably comprises, prior to feeding the liquid solution into the photobioreactor (10), the step of feeding the liquid solution into a heat exchanger (68) for recovering heat from the liquid phase and cooling the same. Moreover, in order to complement this cooling step, and as illustrated in FIG. 2, the photobioreactor (10) of the present invention is preferably provided with at least one cooling tube (70) so as to allow any suitable coolant known to one skilled in the art to flow therein. The cooling tube (70) has an inlet (88) for receiving a coolant and an outlet (not visible) for releasing the same. The cooling tube (70) is preferably disposed between the light-emitting tubes (18). As it will be apparent to one skilled in the art, a casing (90) could be adapted to serve as a cooling tube (70). Such a person in the art will also understand that the cooling tube (70) is advantageously connected to a system that will feed the inlet (88) with a suitable coolant and recirculate the same into the cooling tube (70) for a predefined period of time. Since this kind of system is already known, it will not be described further.

Figure 3:
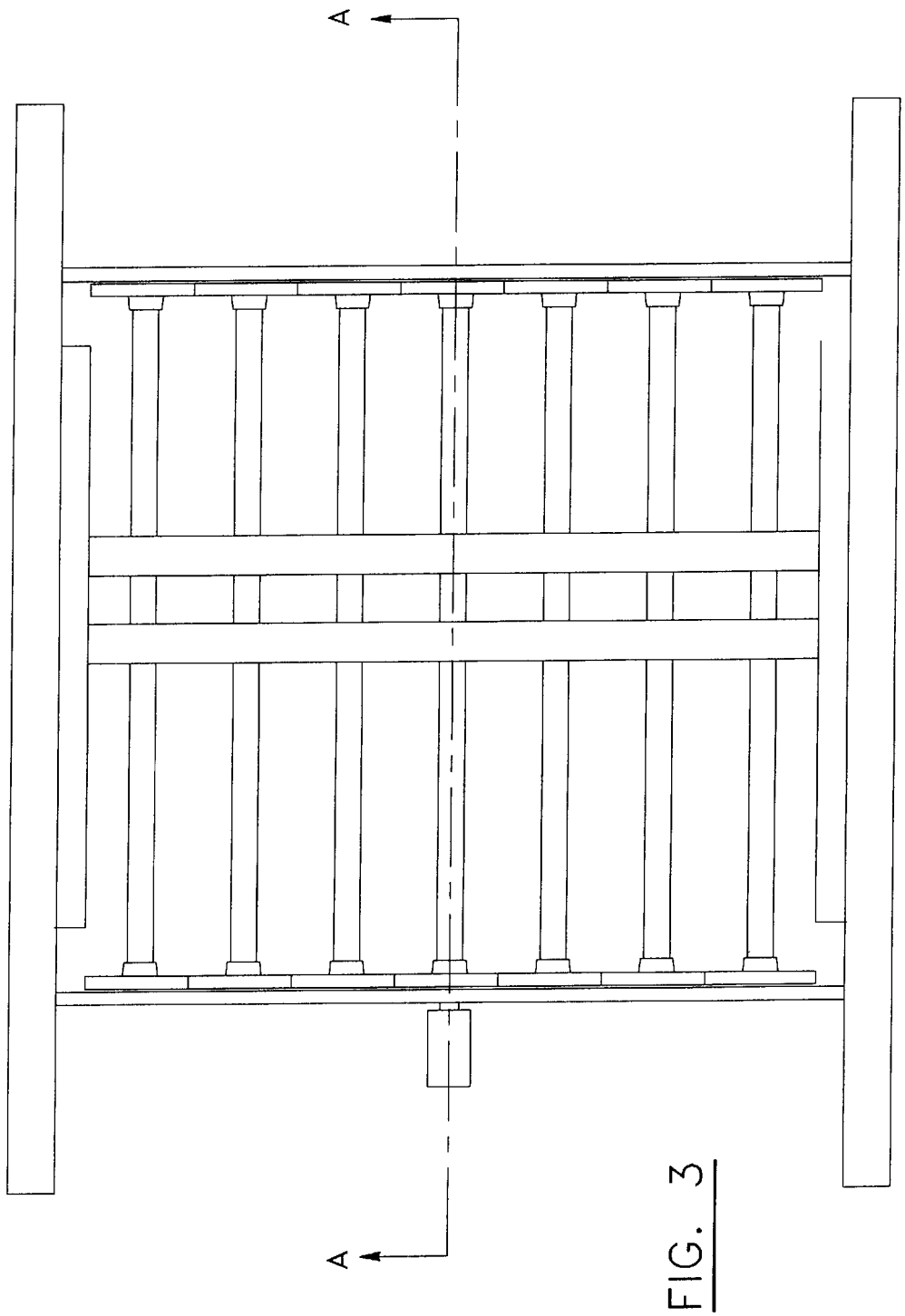
FIG. 3 is a top view of the photobioreactor of FIG. 2.

Referring to FIGS. 2 and 3, in order to carry out the above described process, the present invention further proposes a culture unit (110) for cultivating photosynthetic organisms. The culture unit (110) of the present invention is able to fulfill mainly two roles, namely the culture of photosynthetic organisms and the production of bicarbonate ions as a source of carbon for the growth of the photosynthetic organisms. Therefore, the culture unit (110) of the invention allows the photosynthetic organisms to be cultivated in continuous.

As schematically illustrated in FIG. 8, the culture unit (110) comprises a photobioreactor (10) for cultivating photosynthetic organisms in a liquid culture medium. Such a photobioreactor (10) may be any type of photobioreactor, however, the present invention prefers employing a photobioreactor (10) described above and shown in FIGS. 1 and 2.

The culture unit (110) also comprises a bioreactor (62) for producing bicarbonate ions and hydrogen ions from a $CO_2$-containing gas. As mentioned above, the bioreactor (62) comprises a reaction chamber (64) containing immobilized carbonic anhydrase or analog thereof capable of catalyzing the hydration of dissolved $CO_2$ into the bicarbonate ions and hydrogen ions. The bioreactor (62) will advantageously allow a reduction in the time required to catalyze the transformation of the $CO_2$ into the bicarbonate ions and hydrogen ions. Consequently, the use of the bioreactor (62) helps reducing the size of the equipment required. It also helps increasing the $CO_2$ absorption efficacy.

The bioreactor (62) comprises a liquid inlet (120) in fluid communication with the reaction chamber (64) for receiving a liquid, a gas inlet in fluid communication with the reaction chamber (64) for receiving a $CO_2$-containing gas, and a liquid outlet (122) in fluid communication with the reaction chamber (64) for dispensing a solution containing the bicarbonate ions and hydrogen ions.

The culture unit (110) of the present invention further comprises means for transferring the solution of bicarbonate ions and hydrogen ions dispensed from the liquid outlet (122) to the photobioreactor (10). For example, a pipe system including a pump, or any other suitable means known to a person skilled in the art could be used.

The culture unit (110) preferably comprises means, such as a pump, for removing a portion of the liquid culture from the photobioreactor (10) and means (60) for separating the removed portion of liquid culture into a liquid phase and into a solid phase which contains the organisms. As mentioned above, the separating means is preferably a filter but depending on the type of organisms to grow, other separating means known to one skilled in the art may be used. The culture unit (110) preferably further comprises means for transferring the liquid phase produced in the filter (60) into the liquid inlet (120) of the bioreactor (62). For instance, the liquid phase may be manually transferred to the bioreactor (62) with the use of suitable tools well known by one skilled in the art. Alternatively, the liquid phase could be transferred to the bioreactor (62) with the aid of gravity. Indeed, by placing the filter (60) at a level substantially higher that the one of the bioreactor (62), the liquid phase can be gravity fed into the bioreactor (62).

Furthermore, the culture unit (110) preferably comprises means for adding to the solution of bicarbonate ions and hydrogen ions a concentrate of liquid culture medium. For instance, the concentrate of liquid culture medium can be added to the solution of bicarbonate ions and hydrogen ions by way of manual or gravitational means such as those explained above. Moreover, the culture unit (110) preferably comprises a mixing unit (72), such as a conventional stirrer, for mixing the concentrate of liquid culture medium with the solution of bicarbonate ions and hydrogen ions so as to form a liquid solution. As it will be clear for a person in the art, the liquid solution can be obtained by directly adding the concentrate of liquid culture medium to the solution of bicarbonate ions and hydrogen ions. Alternatively, the concentrate of liquid culture medium and the solution of bicarbonate ions and hydrogen ions can be fed directly to the mixing unit (72) to form the liquid solution.

The culture unit (110) preferably further comprises means, such as a heat exchanger for recovering heat (68) from the liquid solution and cooling the same. Finally, the culture unit (110) preferably further comprises means, such as a pump or any other suitable means for transferring the liquid solution to the photobioreactor (10).

EXAMPLE

The following example is illustrative of the wide range of applicability of the present invention and is not intended to limit its scope. Modifications and variations can be made therein without departing from the spirit and scope of the invention.

Even though the process of the invention as described previously uses only one photobioreactor (10), it will be clear to one skilled in the art from the following example that it is conceivable to use more than one photobioreactor (10) so as to greatly increase the production capacity of the process contemplated by the present invention.

Therefore, a series of fifty (50) photobioreactors of $7,0\,m^3$ can be used for the growth of the microalgae *Spirulina platensis* and for the processing of carbonated water resulting from a bioreactor (62). These photobioreactors (10) are disposed side by side with respect to the second pair of sidewalls (16). Light tubes (22) of the type Cool White of 80 W are used as a light source. The working volume of each photobioreactor (10) is about $3,1\,m^3$. One hundred twenty height (128) light tubes per photobioreactor will contribute to maintain the temperature of the medium at around 36° C. and to provide the necessary source of light.

*Spirulina platensis* is cultivated in a suitable medium. The desired cellular density is about 0,6 gram of algae biomass per liter of culture medium. A working volume of about 3,1 $m^3$ will produce more than 250 kilograms of dry biomass per day. This biomass could be used as a prophylactic agent in the poultry nutrition.

Although preferred embodiments of the present invention have been described in detail herein and illustrated in the accompanying drawings, it is to be understood that the invention is not limited to these precise embodiments and that various changes and modifications may be effected therein without departing from the scope or spirit of the present invention.

What is claimed is:

1. A photobioreactor comprising:
   a container for containing a liquid culture medium for cultivating photosynthetic organisms, a plurality of parallel light-emitting tubes mounted within the container and extending in a first direction, each light-emitting tube having an outer surface;

cleaning means mounted within the container for cleaning the outer surface of the light-emitting tubes; and actuating means for actuating the cleaning means.

2. A photobioreactor as claimed in claim 1, wherein the cleaning means comprises a support frame movable in said first direction, the support frame comprising a plurality of cleaning devices adapted to clean said outer surface of the light-emitting tubes, each of said cleaning devices being associated with a respective one of said light-emitting tubes.

3. A photobioreactor as claimed in claim 2, wherein the support frame comprises at least one plate mounted at right angle to the first direction, said at least one plate comprising a plurality of openings each sized and shaped to receive a respective one of said light-emitting tubes, and each of said cleaning devices being located in a respective one of said openings.

4. A photobioreactor as claimed in claim 3, wherein each of said cleaning devices comprises a brushing means for brushing the outer surface of a respective light-emitting tube.

5. A photobioreactor as claimed in claim 4, wherein the brushing means comprises a plurality of bristles.

6. A photobioreactor as claimed in claim 3, comprising hanging means for hanging the support frame within the container.

7. A photobioreactor as claimed in claim 6, wherein the container has a rectangular configuration with a first and a second pair of opposite sidewalls, the light-emitting tubes extending between said first pair of sidewalls;

the support frame comprises a bottom side, and a top side with two end portions, and the hanging means comprises:

a pair of support members provided respectively on each one of said sidewalls of the second pair of sidewalls; and a pair of resting members, a first one provided on one of said end portion of the top side of the support frame and a second one provided on the other end portion of the top side of the support frame, each of said resting members being respectively adapted to rest on one of said support members and being further movable along the support members.

8. A photobioreactor as claimed in claim 7, wherein said pair of support members comprises a rail mounted on each one of said sidewalls.

9. A photobioreactor as claimed in claim 8, wherein said pair of resting members comprises a roller for rolling on the rail.

10. A photobioreactor as claimed in claim 3, wherein said at least one plate of the support frame is provided with a plurality of through-holes allowing free passage of the culture medium through the plate.

11. A photobioreactor as claimed in claim 1, further comprising a gas dispenser for dispensing $CO_2$ enriched air into the culture medium.

12. A photobioreactor as claimed in claim 11, wherein the gas dispenser comprises at least one dispensing tube spanning generally parallel to the light-emitting tubes underneath the support frame, the dispensing tube comprising a gas inlet for receiving the $CO_2$ enriched air and a plurality of gas outlet for dispensing the $CO_2$ enriched air into the container.

13. A photobioreactor as claimed in claim 12, wherein the support frame comprises a bottom edge comprising brushing means for brushing an outer surface of said at least one dispensing tube.

14. A photobioreactor as claimed in claim 13, wherein the brushing means comprises a plurality of bristles.

15. A photobioreactor as claimed in claim 2, wherein the actuating means comprises a driving endless screw operatively connected to the support frame and a power means for inducing a rotation movement to said endless screw, said rotation movement causing the support frame to move in said first direction.

16. A photobioreactor as claimed in claim 15, wherein said power means is a reversible electric motor or a manual driving handle for imparting the rotation movement to said endless screw.

17. A culture unit for cultivating photosynthetic organisms, comprising:

a photobioreactor as defined in claim 1;

a bioreactor for producing bicarbonate ions and hydrogen ions from a $CO_2$-containing gas, the bioreactor comprising:

a reaction chamber containing immobilized carbonic anhydrase or analog thereof capable of catalyzing the hydration of dissolved $CO_2$ into said bicarbonate ions and hydrogen ions, a liquid inlet in fluid communication with the reaction chamber, for receiving a liquid, a gas inlet in fluid communication with the reaction chamber, for receiving a $CO_2$-containing gas; and a liquid outlet in fluid communication with the reaction chamber, for dispensing a solution containing said bicarbonate ions and hydrogen ions and means for transferring said solution of bicarbonate ions and hydrogen ions dispensed from said liquid outlet to the photobioreactor.

18. A culture unit as claimed in claim 17, comprising means for removing a portion of the liquid culture medium from the photobioreactor and means for separating said portion of the liquid culture medium into a solid phase containing the organisms and into a liquid phase.

19. A culture unit as claimed in claim 18, comprising:

means for transferring the liquid phase obtained in the separating means into the liquid inlet of the bioreactor.

20. A culture unit as claimed in claim 19, comprising:

means for adding to said solution of bicarbonate ions and hydrogen ions a concentrate of liquid culture medium.

21. A culture unit as claimed in claim 20, comprising:

a mixing unit for mixing said concentrate of liquid culture medium with the solution of bicarbonate ions and hydrogen ions so as to obtain a liquid solution.

22. A culture unit as claimed in claim 21, comprising means for recovering heat from the liquid solution and cooling the same.

23. A culture unit as claimed in claim 22, comprising:

means for transferring said liquid solution to the photobioreactor.

24. A process for producing photosynthetic organisms, the process comprising the steps of:

a) cultivating a photosynthetic organism in a photobioreactor as defined in claim 1, and thereby obtaining a liquid culture medium containing photosynthetic organisms;

b) removing from said photobioreactor a portion of said liquid culture medium; and c) separating the liquid culture medium of step b) into a solid phase containing the photosynthetic organisms and a liquid phase.

25. A process as claimed in claim 24, further comprising the steps of):
   producing a solution of bicarbonate ions and hydrogen ions in a bioreactor comprising a reaction chamber containing immobilized carbonic anhydrase or analog thereof capable of catalyzing the hydration of dissolved $CO_2$ into bicarbonates ions and hydrogen ions; and
   feeding the photobioreactor with the solution of bicarbonates ions and hydrogen ions produced in the bioreactor.

26. A process as claimed in claim 25, comprising the step of:
   feeding the bioreactor with the liquid phase obtained in step c).

27. A process as claimed in claim 26, wherein step c) of separating comprises a process selected from the group consisting of filtration, flocculation, sedimentation and centrifugation.

28. A process as claimed in claim 27, comprising, prior to the step of feeding the photobioreactor the step of:
   adding to said solution of bicarbonates ions and hydrogen ions a concentrate liquid culture medium, and thereby forming a liquid solution.

29. A process as claimed in claim 28, comprising the step of feeding said liquid solution into a heat exchanger for recovering heat from the liquid solution and cooling the same.

* * * * *